(12) United States Patent
Liu et al.

(10) Patent No.: US 10,196,417 B2
(45) Date of Patent: Feb. 5, 2019

(54) BAICALIN MAGNESIUM COMPOUND AND ITS PREPARATION METHOD AND APPLICATION

(71) Applicant: CHENGDE MEDICAL UNIVERSITY, Chengde, Hebei (CN)

(72) Inventors: Cuizhe Liu, Hebei (CN); Zhixuan Wang, Hebei (CN); Ceyu Miao, Hebei (CN); Liyan Liu, Hebei (CN); Hefei Xue, Hebei (CN); Xigang Liu, Hebei (CN); Wenshan Du, Hebei (CN); Yixin Liu, Hebei (CN); Lin Zhang, Hebei (CN); Xiaoxia Mao, Hebei (CN); Jinjun Liu, Hebei (CN); Guiqin Zhao, Hebei (CN)

(73) Assignee: CHENGDE MEDCIAL UNIVERSITY, Chengde (CN)

( * ) Notice: Subject to any disclaimer, the term of this patent is extended or adjusted under 35 U.S.C. 154(b) by 0 days.

(21) Appl. No.: 16/052,419

(22) Filed: Aug. 1, 2018

(65) Prior Publication Data
US 2018/0346503 A1 Dec. 6, 2018

Related U.S. Application Data

(63) Continuation of application No. PCT/CN2017/071616, filed on Jan. 19, 2017.

(30) Foreign Application Priority Data

Feb. 1, 2016 (CN) .......................... 2016 1 0068926

(51) Int. Cl.
  *C07H 17/07* (2006.01)
  *C07H 1/08* (2006.01)
(52) U.S. Cl.
  CPC .............. *C07H 17/07* (2013.01); *C07H 1/08* (2013.01)

(58) Field of Classification Search
None
See application file for complete search history.

(56) References Cited

U.S. PATENT DOCUMENTS

2005/0215494 A1* 9/2005 Yuen .................... A61K 31/382
                                                                514/27

FOREIGN PATENT DOCUMENTS

CN              105061538 A      11/2015

OTHER PUBLICATIONS

Ning Wong et al ,WANGNing Interaction Betwen Scutellaria baicalensis Georgi and Human Serum Albumin , Feb. 28, 2011.
Bi , Shuyun et al , Investigation of the interaction between flavonoids and human serum albumin, Dec. 31, 2004.

* cited by examiner

Primary Examiner — Traviss C McIntosh, III
(74) Attorney, Agent, or Firm — Wayne & Ken, LLC; Tony Hom

(57) ABSTRACT

A baicalin magnesium compound and methods for preparing and extracting the same. The method for preparing the baicalin magnesium compound includes steps of preparation of a baicalin suspension, preparation of a magnesium ion-containing suspension, reaction and drying. The method for extracting the baicalin magnesium compound includes steps of pretreatment of macroporous resin, extraction, adsorption and elution, concentration and drying and purification. The methods restores the baicalin to the original form as found in radix scutellariae, and the baicalin magnesium compound may be used as a substitute for the baicalin in pharmaceutical applications. As compared to the baicalin, the baicalin magnesium has a greatly increased solubility, faster adsorption rate and higher oral bioavailability. The baicalin magnesium compound may also be easily formulated as a water-soluble injection or a powder injection. Pharmacological tests show that the baicalin magnesium compound is more pharmacologically active than the baicalin.

12 Claims, 2 Drawing Sheets

BAICALIN MAGNESIUM COMPOUND AND ITS PREPARATION METHOD AND APPLICATION

CROSS-REFERENCE TO RELATED APPLICATIONS

This application is a continuation of International Application No. PCT/CN2017/071616 with a filing date of Jan. 19, 2017, designating the United States, now pending, and further claims priority to Chinese application no. 201610068926.3 with a filing date of Feb. 1, 2016. The content of the aforementioned applications, including any intervening amendments thereto, are incorporated herein by reference.

TECHNICAL FIELD

The present invention is directed to pharmaceuticals. More particularly, the present invention relates to a baicalin magnesium compound, methods for producing the baicalin magnesium compound, and an application of the baicalin magnesium compound.

BACKGROUND OF THE PRESENT INVENTION

Radix scutellariae, first published in *Shen Nong's Herbal Classic*, is the dry root of *Scutellaria baicalensis* Georgi, Labiatae family, effective in clearing away pathogenic heat and dampness, purging intense fire and detoxicating, facilitating hemostasis and preventing miscarriage. Baicalin is a flavonoid compound with a molecular formula of $C_{21}H_{18}O_{11}$, which is more than 9% by weight or even up to 20% by weight in radix scutellariae and is one of main active ingredients of radix scutellariae.

Modern pharmacological researches have indicated that baicalin plays a role in eliminating oxygen free radicals, antiarrhythmia, dilating heart and cerebral vessels, reducing blood pressure and keeping calm, protecting liver and gallbladder and anti-pathogen, and also inhibits tumors such as prostate cancer, cervical cancer, lung cancer, malignant lymphoma, myeloma and liver cancer. Clinically, there have been various preparations such as baicalin tablets and baicalin capsules, which are mainly used for treating acute and chronic hepatitis, cardiovascular diseases and the like.

Magnesium is an element essential for the activities of normal life and metabolism of living organisms. Magnesium affects various biological functions of cells including transport of potassium ions and calcium ions, regulation of cell signaling, energy metabolism, protein and nucleic acid synthesis; activation and inhibition of catalyticase; and regulation of cell cycle, cell proliferation and cell differentiation. Also, magnesium participates in maintaining genomic stability and is associated with oxidative stress and tumorigenesis in the body.

Baicalin is soluble in alkaline solutions such as sodium hydroxide, sodium carbonate and sodium bicarbonate, but it is unstable in alkaline liquor and will gradually turn to dark brown. It is slightly soluble in hot glacial acetic acid, hardly soluble in methanol, ethanol and acetone and insoluble in water, benzene, ether and chloroform. Since baicalin is almost insoluble in water, oral bioavailability of baicalin is low, so that the clinical application of baicalin is greatly limited.

Recently, there are many related reports on the use of new preparation techniques to improve the solubility and bioavailability of baicalin, involving the preparation of baicalin into metal complexes, β-cyclodextrin inclusion compounds, solid dispersions, phospholipid complexes, microparticles, nanoparticles, liposome nanoemulsions, microemulsions, gelatin microspheres, and the like.

As described in *Chinese Pharmacopeia* under Radix Scutellariae Extract (2015, Part I), baicalin is obtained through water extraction and acid precipitation and purification through alkali-soluble acid precipitation. The commercially available baicalin is generally prepared by this method. Baicalin is found in radix scutellariae as a magnesium salt. This form of baicalin has good water solubility and may be extracted by water dissolution. However, the original structure of the baicalin will be damaged by acid precipitation, resulting in low water solubility, slow adsorption rate and low baicalin bioavailability, as well as reduced baicalin efficacy.

The present invention provides a method for extracting baicalin magnesium from radix scutellariae without changing the original form of baicalin as found in radix scutellariae, and further provides a method for synthesizing baicalin magnesium using the commercially available baicalin as raw material, in a manner that the baicalin is returned to its original form existed in the radix scutellariae. The baicalin magnesium can be used as a substitute for the baicalin. Baicalin magnesium has greatly increased solubility, faster adsorption rate and higher oral bioavailability as compared to the baicalin. The baicalin magnesium can also be easily formulated as a water-soluble injection or a powder injection. Moreover, the compound can also display the synergistic pharmacological actions of baicalin and magnesium ions, thereby enhancing the efficacy.

The present invention is designed on the basis of a large number of experiments and analysis.

SUMMARY OF THE PRESENT INVENTION

Technical Problem to be Solved

An objective of the present invention is to provide a baicalin magnesium compound.

Another objective of the present invention is to provide a method for producing the baicalin magnesium compound.

Yet another objective of the present invention is to provide an application of the baicalin magnesium compound.

Technical Solutions

The present invention provides a baicalin magnesium compound of formula (I):

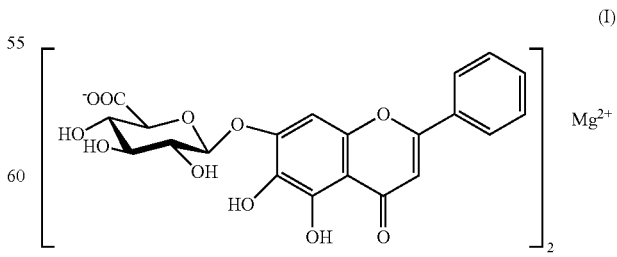

(I)

The present invention further provides a method for preparing the baicalin magnesium compound including the following steps:

a. adding baicalin powder to purified water at a weight (g)-volume (ml) ratio of 1:20-100 of the baicalin to the purified water; and uniformly mixing the same to obtain a baicalin suspension;

b. adding a magnesium compound in the baicalin suspension obtained in step A at a molar ratio of baicalin to magnesium of 0.5-3.0:1; and uniformly mixing the same to obtain a magnesium ion-containing baicalin suspension;

c. reacting the magnesium ion-containing baicalin suspension obtained in step B at 20-70° C. under stirring until the reaction becomes clear; and then filtering the magnesium ion-containing baicalin suspension to obtain a filtrate; and d. drying the filtrate obtained in step C to produce the baicalin magnesium compound.

In a preferred embodiment of the present invention, the magnesium compound is selected from the group consisting of magnesium hydroxide, magnesium oxide, basic magnesium carbonate, magnesium acetate, magnesium sulfate, magnesium nitrate and magnesium chloride.

The present invention further provides another method for preparing the baicalin magnesium compound including the following steps:

a. soaking a macroporous resin in a 95 vol % ethanol solution for 20-28 hours; packing the soaked macroporous resin on a column in a wet manner to allow the 95 vol % ethanol solution to pass through macroporous resin column at a rate of 1.5-2.5 BV/h until a liquid from the macroporous resin column and water mixed at a ratio of 1:5 by volume is no longer white and cloudy; and eluting the macroporous resin column to colorless with distilled water at a flow rate of 1.5-2.5 BV/h;

b. adding radix scutellariae in a 40-60 vol % ethanol solution at a weight (g)-volume (ml) ratio of 1:8-15 of the radix scutellariae to the 40-60 vol % ethanol solution under stirring at 55-65° C. for 0.8-1.2 hours to produce a mixture; separating the mixture to obtain a solution and a residue; repeatedly subjecting the residue to extraction 2-3 times under the same conditions to produce multiple extracts; and combining the multiple extracts to obtain a radix scutellariae extract;

c. passing the radix scutellariae extract obtained in step B through the macroporous resin column in step A at a rate of 1.5-2.5 BV/h for adsorption; washing the macroporous resin column with water of 4-6 times the volume of a macroporous resin bed; and eluting the macroporous resin column with 45-55 vol % ethanol solution of 4-6 times the volume of the macroporous resin bed to collect a baicalin-containing eluent;

d. concentrating the baicalin-containing eluent obtained in step C at 35-65° C. under reduced pressure until a concentrate has a volume of 1-15 times the weight in grams of the radix scutellariae; and drying the concentrate to obtain a crude baicalin magnesium extract; and e. purifying the crude baicalin magnesium extract obtained in step D to produce the baicalin magnesium compound.

In another preferred embodiment of the present invention, the macroporous resin is selected from the group consisting of HPD-100, AB-8, D101 and YWD06B.

In another preferred embodiment of the present invention, the macroporous resin has a particle size of 10-80 mesh.

In another preferred embodiment of the present invention, a ratio of diameter to height of the macroporous resin column is 1:3-8.

In another preferred embodiment of the present invention, the drying process is heating to evaporate, spray drying or freeze drying.

In another preferred embodiment of the present invention, the baicalin magnesium compound is further purified by recrystallization, octadecylsilane reversed-phase column chromatography or preparative liquid chromatography until the baicalin magnesium compound has a content of 95% by weight or more.

The present invention further provides an application of the baicalin magnesium compound. The baicalin magnesium compound is used for the preparation of drugs for treating liver injury, cerebral ischemia, diabetes mellitus, inflammations or tumors, by substituting the radix scutellariae or baicalin with a equivalent dose in a single drug or compound preparation of the traditional Chinese medicine. The baicalin magnesium compound can also be easily formulated as a water-soluble injection or a powder injection.

The present invention will be described below in more detail.

The present invention provides a baicalin magnesium compound as presented by formula (I):

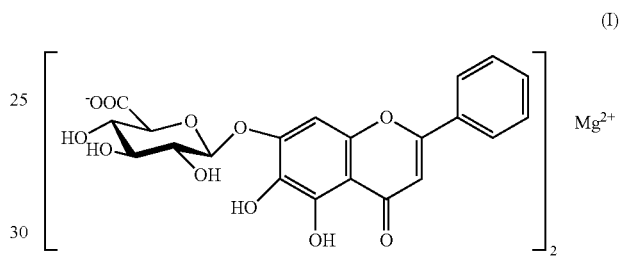

The present invention further provides a method for preparing the baicalin magnesium compound.

The present invention provides a method for extracting baicalin magnesium from radix scutellariae, and further provides a method for synthesizing baicalin magnesium using the commercially available baicalin as raw material. In these methods, the original form of baicalin in the radix scutellariae is not changed, so that the baicalin magnesium can be used as a substitute for the baicalin in pharmaceuticals. Baicalin magnesium has greatly increased solubility, faster adsorption rate and higher oral bioavailability as compared to baicalin. The baicalin magnesium compound can also be easily formulated as a water-soluble injection or a powder injection. Moreover, the compound can also display the synergistic pharmacological actions of baicalin and magnesium ions, thereby enhancing the efficacy.

The method for preparing the baicalin magnesium includes the following steps:

a. adding baicalin powder to purified water at a weight (g)-volume (ml) ratio of 1:20-100 of the baicalin to the purified water; and uniformly mixing the same to obtain a baicalin suspension;

b. adding a magnesium compound in the baicalin suspension obtained in step A at a molar ratio of baicalin to magnesium of 0.5-3.0:1; and uniformly mixing the same to obtain a magnesium ion-containing baicalin suspension;

c. reacting the magnesium ion-containing baicalin suspension obtained in step B at 20-70° C. under stirring until the reaction becomes clear; and then filtering the magnesium ion-containing baicalin suspension to obtain a filtrate; and d. drying the filtrate obtained in step C to produce the baicalin magnesium compound.

In step A, the baicalin is used as a raw material, which is commercially available. The ratio of the baicalin to the purified water is 1:20-100, preferably 1:30-70, and more preferably 1:32-36. When the ratio of the baicalin to the purified water is greater than 1:20, the concentration of the baicalin suspension is too high to bring about many impurities due to incomplete reaction; however, when the ratio of the baicalin to the purified water is less than 1:100, the reaction rate of magnesium ion-containing baicalin suspension is slow, bringing about many impurities due to incomplete reaction.

In step B, the magnesium compound is selected from the group consisting of magnesium hydroxide, magnesium oxide, basic magnesium carbonate, magnesium acetate, magnesium sulfate, magnesium nitrate and magnesium chloride, which are commercially available. Preferably, the magnesium compound is magnesium hydroxide, magnesium oxide or basic magnesium carbonate. More preferably, the magnesium compound is magnesium hydroxide.

In step B, the molar ratio of baicalin to magnesium is 0.5-3.0:1; preferably 0.8-2.6:1; and more preferably 1.8-2.2:1. When the molar ratio of baicalin to magnesium is less than 0.5:1, there will be many remaining magnesium ions in the reaction, which form impurities in the resulting product; however, when the molar ratio of baicalin to magnesium is greater than 3.0:1, the amount of the baicalin is too high resulting in lower reaction rate, and thus it is difficult to filter the magnesium ion-containing baicalin suspension due to many impurities.

In step C, the baicalin is reacted with the magnesium compound in the magnesium ion-containing baicalin suspension to generate baicalin magnesium, that is in a reaction medium, $Mg^{2+}$ from the magnesium compound is bonded to $COO^-$ from the baicalin to generate the baicalin magnesium. A temperature at which the baicalin reacts with the magnesium compound is 20-70° C.; preferably, 40-65° C.; and more preferably 50-60° C. When the temperature is lower than 20° C., the reaction is too slow, resulting in too many impurities; however, when the temperature is higher than 70° C., the baicalin will be decomposed.

In step C, the reaction progress is determined by whether the reaction system becomes clear and transparent, because the reaction is a precipitation reaction producing a precipitate and a resulting product which is dissolved in the reaction system. The reaction is completed when it becomes clear.

In step C, filtration is to remove residues that are not completely reacted in the reaction system, or other impurities without participating in the reaction.

A filter unit for the filtration may be various filter units which are usually used in pharmaceuticals and chemical industries; for example, a vacuum filter, a plate-and-frame filter press and the like.

In step D, the drying process is heating to evaporate, spray drying or freeze drying.

The heating to evaporate should be interpreted as heating to evaporate the moisture in the filtrate obtained in step C to produce a baicalin magnesium compound having a moisture content of 1.0% or less by weight, which is determined by oven drying.

The spray drying should be interpreted as dispersing the filtrate obtained in step C into particles by a spray drying device and bringing the particles into contact with hot air to instantly remove moisture so as to obtain the baicalin magnesium compound having a moisture content of 1.0% or less by weight. The spray drying device is commercially available, for example, a product under the trade name QZR-5 (Linzhou Drying Machine Company, Xishan, Jiangsu).

The freeze drying should be interpreted as freezing the filtrate obtained in step C to 0° C. or less by a freeze-drying device and sublimating moisture from solid to vapor by heating under high vacuum to remove the moisture so as to obtain the baicalin magnesium compound having a moisture content of 1.0% or less by weight. The freeze-drying device is commercially available, for example, a product under the trade name LGJ-22D (Beijing Four-Ring Scientific Instrument Co., Ltd.).

The present invention further provides another method for preparing the baicalin magnesium compound including the following steps:

a. soaking a macroporous resin in a 95 vol % ethanol solution for 20-28 hours; packing the soaked macroporous resin on a column in a wet manner to allow the 95 volume % ethanol solution to pass through macroporous resin column at a rate of 1.5-2.5 BV/h until a liquid from the macroporous resin column and water mixed at a ratio of 1:5 by volume is no longer white and cloudy, and eluting the macroporous resin column to colorless with distilled water at a flow rate of 1.5-2.5 BV/h;

b. adding radix scutellariae in a 40-60 vol % ethanol solution at a weight (g)-volume (ml) ratio of 1:8-15 of the radix scutellariae to the 40-60 vol % ethanol solution and stirring at 55-65° C. for 0.8-1.2 hours to produce a mixture; separating the mixture to obtain a solution and a residue; repeatedly subjecting the residue to extraction 2-3 times under the same conditions to produce multiple extracts; and combining the multiple extracts to obtain a radix scutellariae extract;

c. passing the radix scutellariae extract obtained in step B through the macroporous resin column in step A at a rate of 1.5-2.5 BV/h for adsorption; washing the acroporous resin column with water of 4-6 times the volume of a macroporous resin bed; and eluting the macroporous resin column with 45-55 vol % ethanol solution of 4-6 times the volume of the macroporous resin bed to collects baicalin-containing eluent;

d. concentrating the baicalin-containing eluent c obtained in step C at 35-65° C. under reduced pressure until a concentrate has a volume is 1 to 15 times the weight in grams of the radix scutellariae; and drying the concentrate to obtain a crude baicalin magnesium extract; and e. purifying the crude baicalin magnesium extract obtained in step D to obtain the baicalin magnesium compound. in step e, the baicalin magnesium compound is purified by recrystallization, octadecyl silane reversed-phase column chromatography or preparative liquid chromatography until the baicalin magnesium compound has a content of 95% by weight or more.

The macroporous resin should be interpreted as a polymer capable of concentrating and separating the baicalin magnesium compound in the filtrate obtained in step C, also referred to as a polymer adsorbent.

The macroporous resin is selected from HPD-100, AB-8, D101 or YWD06B.

HPD-100 macroporous resin is a non-polar styrene copolymer suitable for extraction and separation of natural products, such as saponins, flavonoids and terpenes, and plants. The HPD-100 macroporous resin used herein is provided by Zhengzhou Qinshi Science & Technology Co., Ltd.

AB-8 macroporous resin is a low-polar styrene copolymer suitable for extraction, separation or purification of low-polar substances such as steviosides and alkaloids. The AB-8 macroporous resin used herein is provided by Zhengzhou Qinshi Science & Technology Co., Ltd.

D-101 macroporous resin is a non-polar styrene copolymer which is a polymer adsorbent of a porous spongy structure, and suitable for separation of saponins, flavonoids and alkaloids. The D-101 macroporous resin used herein is aprovided by Zhengzhou Xidian Electric Power Resin Sales Co., Ltd.

YWD06B macroporous resin is mainly used for extraction of bilirubins, alkaloids and flavonoids as well as tea polyphenol, soy isoflavone, epimedium flavone and astragalin. The YWD06B macroporous resin used herein is provided by Zhengzhou Qinshi Science & Technology Co., Ltd.

Pretreatment of the macroporous resin is to remove the floating impurities and inert organic reagents from the macroporous resin.

The macroporous resin used herein has a particle size of 10-80 mesh.

The ratio of the diameter to the height of the macroporous resin column is 1:3-8.

In step B, an ethanol solution is used to extract baicalin from radix scutellariae. When the ratio of the baicalin to the ethanol solution is greater than 1:8, the extract concentration is too high and the extraction is incomplete; however, when the ratio of the baicalin to the ethanol solution is less than 1:15, the extract has a large volume and undesirable adsorption in the macroporous resin with impurities in the eluent. The ratio of the baicalin to the ethanol solution is 1:8-15, preferably, 1:9-12, and more preferably 1:9.6-10.4.

The concentration of the ethanol solution used for extracting the baicalin magnesium compound is 40-60% by volume; preferably 44-56% by volume; and more preferably 48-52% by volume. When the concentration of the ethanol solution is less than 40%, there will be many impurities in the extract; however, when the concentration of the ethanol solution is greater than 60%, the extraction rate of the baicalin magnesium compound will be reduced.

The temperature for extracting the baicalin magnesium compound is 55-65° C., preferably 57-63° C., and more preferably 58-62° C. When the temperature is less than 55° C., the extraction of the baicalin magnesium compound may be incomplete; however, when the temperature is greater than 65° C., the decomposition of the baicalin magnesium compound may occur.

The stirring rate may be selected based on actual needs, which is not difficult for those skilled in the art.

The extraction device used in this extraction step is an extractor and concentrator set, a hot reflux extractor set, a static extractor set or an electric/steam multifunctional extractor set, which are commercially available, for example, a product under the trade name nR.ZN20A (Changshu Traditional Chinese Medicine Pharmaceutical Machinery Company, Jiangsu).

In step C, the rate of the radix scutellariae extract passing through the macroporous resin column is 1.5-2.5 BV/h; preferably 1.7-2.3 BV/h; and more preferably 1.9-2.1 BV/h. When the rate is less than 1.5 BV/h, the baicalin is adsorbed onto the macroporous resin and thus is difficult to elute; however, when the rate is greater than 2.5 BV/h, the baicalin is not well separated from the impurities, bringing about more impurities in the eluent.

In step C, washing is to remove the impurities. The volume of the washing water should not exceed the above range otherwise it is possible to cause loss of the baicalin magnesium compound.

The macroporous resin column is eluted with an 45-55 vol % ethanol solution of 4-6 times the volume of a macroporous resin bed, and a baicalin-containing eluent is collected.

In step D, the eluent is concentrated under a reduced pressure of 0.01-0.1 Mpa at 35-65° C. Equipment for concentration under a reduced pressure is commercially available, for example, R2002 rotary evaporator (Shanghai Shenshun Biotechnology Co., Ltd). Description for the drying, as described above, is omitted.

In step E, the purification by recrystallization is performed with an ethanol-water (1:9 to 9:1) solvent in a water bath at 60° C.

The octadecyl silane (ODS) reversed-phase column chromatography is commonly used, also referred to as C18 column chromatography. Due to its long-chain alkyl bonded phase, higher carbon content and better hydrophobicity, the ODS reversed-phase column chromatography has higher adaptability to various types of biomacromolecules and thus is most widely used in the biochemical analysis.

Purification by ODS column chromatography is performed using 10-40% of methanol-water as eluent with GEL C18AAG12S50 ODS Column (YMC Company).

Purification by preparative liquid chromatography is performed with CTO-10A Preparative Liquid Phase (Shimadzu Corporation), where the liquid phase is methanol-water (30:70).

The content of the baicalin magnesium compound is measured by high performance liquid chromatography with Agilent 1260, Aglient 5HC C18(2) chromatographic column and liquid phase of methanol-water (40:60).

According to a equilibrium solubility method, the solubility of baicalin and baicalin magnesium in water at 37° C. was 0.058 mg/mL and 129.1 mg/mL, respectively. This shows that the baicalin magnesium compound has better water solubility than baicalin and can be used for preparing a water-soluble injection or a powder injection.

The baicalin magnesium compound prepared by the above two methods will be analyzed below in detail in terms of its structure by a chemical analysis method.

I. Ultraviolet Absorption Spectrum Analysis

Agilent 8453 Device is used for the ultraviolet absorption spectrum analysis.

The maximum absorption wavelength is automatically scanned by Agilent 8453 under 200 nm to 760 nm.

The ultraviolet absorption spectrum is measured by a comparison method with control.

2 mg of baicalin and 2 mg of baicalin magnesium prepared in the present invention are respectively dissolved in 10 ml of methanol, and the maximum adsorption wavelengths are measured. The results are shown in Table 1.

TABLE 1

Maximum adsorption wavelengths of baicalin and baicalin magnesium

| Compounds | Maximum adsorption wavelength | | |
|---|---|---|---|
| Baicalin | 216 nm | 276 nm | 317 nm |
| Baicalin Magnesium | 216 nm | 276 nm | 317 nm |

It can be known from Table 1 that the baicalin and the baicalin magnesium compound both have maximum ultraviolet absorption wavelengths (λmax) at 216 nm, 276 nm and 317 nm, which indicates that the magnesium ions have little influence on the delocalization resonance structure of the baicalin. However, if $Mg^{2+}$ is bonded to the 4-carbon atom and the 5-phenolic hydroxyl group of the baicalin, the degree of delocalization of electrons in the molecule will be increased. As a result, the energy required by electron transition is reduced, and red shift of the adsorption peak will occur. Therefore, the results indicate that $Mg^{2+}$ is less likely to coordinate with C4 and C5 of the baicalin.

II. Infrared Absorption Spectroscopy

TENSOR27 BRUKER Fourier Transform Infrared Spectrometer is used for the Infrared absorption spectrum analysis.

The infrared absorption spectrum is measured by a conventional potassium bromide pellet technique.

Generally, for alcohol and phenol, the absorption peak of a free —OH bond is at 3650-3580 cm$^{-1}$; the absorption peak of an associated —OH bond is at 3400-3200 cm$^{-1}$; and the absorption peak of a carboxylic —OH bond is at 3540-3350 cm$^{-1}$. The baicalin has a wide and strong peak at 3390 cm$^{-1}$, which may be the stretching vibration peak of —OH in this molecule; while the peak intensity of the baicalin magnesium at 3390 cm$^{-1}$ is weakened obviously. Therefore, it is indicated that the hydrogen bond in the molecule has been damaged.

Generally, the C=O absorption peak is at 1850-1600 cm$^{-1}$. In the infrared spectrum of the baicalin, the carbonyl absorption peak on glucuronic acid is at 1727 cm$^{-1}$; but such peak will disappear after the compound is formed. The absorption peak of C=O at 4-position is at 1660 cm$^{-1}$, and the stretching vibration absorption peak of C—O at 5-position is at 1202 cm$^{-1}$, which have no obvious change after the compound is formed. The absorption peak of the benzene ring skeleton at 1600 cm$^{-1}$ to 1400 cm$^{-1}$ also remains unchanged. It is indicated that the reaction product has no influence on the benzene ring conjugated system. By analysis and comparison of the main feature peaks of the infrared spectra of the baicalin and the baicalin magnesium, it is indicated that the baicalin reacts with Mg$^{2+}$ on the carboxyl group of the glucuronic acid. The infrared spectrum peaks of the baicalin and the baicalin magnesium are shown in the following Table 2.

TABLE 2

Assignment of the infrared spectrum peaks of the baicalin and the baicalin magnesium

| Compounds | υ5-OH | υ4-C=O | υ4-C—O | υ6''-C=O |
|---|---|---|---|---|
| Baicalin | 3391 | 1660 | 1202 | 1727 |
| Baicalin Magnesium | 3384 | 1660 | 1197 | — |

III. $^1$H and $^{13}$C-NMR

VARIAN INOVA 600 NMR Spectrometer is used for NMR analysis.

Deuterated DMSO is used as a solvent for measurement of $^1$H and $^{13}$C-NMR.

$^1$H and $^{13}$C-NMR data (DMSO) of baicalin, synthetic baicalin magnesium and the baicalin magnesium compound extracted from radix scutellariae is listed in Table 3.

TABLE 3

NMR data of baicalin and baicalin magnesium

| Number | Baicalin | Baicalin Magnesium | Number | Baicalin | Baicalin Magnesium |
|---|---|---|---|---|---|
| C-2 | 163.5 | 163.5 | 6''-OH | 12.7 | — |
| C-3 | 104.7 | 104.7 | 5-OH | 12.577 | 12.562 |
| C-4 | 182.5 | 182.5 | 6-0H | 8.647 | 8.646 |
| C-5 | 149.2 | 149.1 | H-2', 6' | 8.069 | 8.098 |
| C-6 | 132.0 | 132.0 | H-3', 4', 5' | 7.567-7.613 | 7.565-7.588 |
| C7 | 151.2 | 151.4 | H-8 | 7.037 | 7.034 |
| C-8 | 93.7 | 93.9 | H-3 | 6.990 | 6.983 |
| C-9 | 146.8 | 146.7 | 2'', 3'', 4''-H | 5.230-5.486 | 5.157-5.455 |
| C-10 | 106.1 | 106.1 | H-1'' | | |
| C-1' | 130.8 | 130.8 | H-5'' | 4.06 | 3.93 |
| C-2', 6' | 126.3 | 126.3 | H-2'', 3'', 4'' | 3.319-3.448 | 3.322-3.387 |
| C-3', 5' | 129.1 | 129.1 | | | |
| C-4' | 130.6 | 130.6 | | | |
| C-1'' | 99.9 | 100.1 | | | |
| C-2'' | 72.8 | 72.8 | | | |
| C-3'' | 75.2 | 75.1 | | | |
| C-4'' | 71.3 | 71.4 | | | |
| C-5'' | 75.4 | 75.4 | | | |
| C-6'' | 170.0 | 170.4 | | | |

Conclusion $^{13}$C-NMR of baicalin shows a total of 21 C signals. Comparison between $^{13}$C-NMR of baicalin magnesium and $^{13}$C-NMR of baicalin shows that the number of absorption peaks, the chemical shift, the number of split peaks and the coupling constant are very close, indicating that the introduction of Mg$^{2+}$ has little influence on the nuclear spin of $^{13}$C the baicalin, and Mg$^{2+}$ is less likely to bind to C4 and C5 of baicalin.

In the $^1$H-NMR spectrum, 12.5 is hydrogen on —OH at 5-position, and 12.7 is active hydrogen of carboxyl group on glucuronic acid. After the magnesium compound is formed, 12.5 still exists, but 12.7 disappears. The number of $^1$H absorption peaks, the chemical shift, the number of split peaks and the coupling constant are very close, indicating that Mg$^{2+}$ binds to baicalin at carboxyl group of glucuronic acid.

IV. Mass Spectrum Analysis

Agilent 6310 Device is used for mass spectrum analysis.

Mass spectrometry conditions: ESI source; mobile phase: acetonitrile; MS 2; and scanning range: 100 to 2000.

The results of the mass spectrum analysis are as follows: molecular ion peak M/Z: 914.9;

M/Z: 2701.7, indicating the presence of relatively complete baicalin aglycone ($C_{15}H_{10}O_5$) fragments;

M/Z: 446.7, indicating the presence of baicalin ($C_{21}H_{18}O_{11}$) fragments; and M/Z: 468.6, indicating the presence of baicalin magnesium ($C_{21}H_{17}O_{11}Mg$) fragments.

V. Elemental Analysis and Atomic Absorption Analysis

P.E 2400 elemental analyzer 2400 II is used for the elemental analysis.

SHIMADZU AA-7000 Spectrophotometer is used for the atomic absorption analysis.

The atomic absorption analysis is performed by a standard curve method using a conventional flame atomic absorption spectrophotometry.

The results of the elemental analysis and the atomic absorption analysis of the synthesized baicalin magnesium are listed in the following Table 4.

TABLE 4

Results of elemental analysis and atomic absorption analysis of the synthesized baicalin magnesium

| Elements | Measured W % | Theoretical W % |
|---|---|---|
| C | 55.14 | 55.14 |
| H | 3.79 | 3.72 |
| Mg | 2.56 | 2.62 |

The above results indicate that $Mg^{2+}$ reacts with two carboxyl groups on the glucuronic acid of the baicalin; the molecular weight is 914; and the molecular formula is $Mg(C_{21}H_{17}O_{11})_2$.

The present invention further provides an application of the baicalin magnesium. The baicalin magnesium compound is used for the preparation of drugs for treating liver injury, cerebral ischemia, diabetes mellitus, inflammations or tumors, by substituting the radix scutellariae or baicalin with a equivalent dose in a single drug or compound preparation of the traditional Chinese medicine.

In the method for preparing baicalin magnesium of the present invention, no acid or alkali is added, and thus the original form of the baicalin found in the radix scutellariae is not be damaged. no toxic and harmful organic reagent is used which is green and environmentally friendly, and the resulting product has high purity.

By means of ultraviolet spectroscopy, infrared spectroscopy, atomic absorption spectrometry, HNMR hydrogen spectroscopy, carbon spectroscopy and liquid chromatography-mass spectrometry, it is proved that the baicalin magnesium extracted from the radix scutellariae and the baicalin magnesium prepared with the commercially available baicalin through reactions are consistent in structure. Pharmacokinetic experiments show that the baicalin magnesium has faster adsorption rate and higher oral bioavailability than the baicalin. Pharmacological experiments show that the baicalin magnesium has higher pharmacological activity.

Beneficial Effects by the method for extracting baicalin magnesium of the present invention, the original form of the baicalin found in the radix scutellariae is not be damaged which is green and environmentally friendly, and the resulting product has high purity. The synthetic process is simple and controllable in quality, and can restore the baicalin to the original form found in the radix scutellariae. The baicalin magnesium has greatly increased solubility, faster adsorption rate and higher oral bioavailability. The baicalin magnesium can be used as a substitute for the baicalin in pharmaceuticals. The baicalin magnesium can also be easily formulated as a water-soluble injection or a powder injection. Pharmacological experiments show that the baicalin magnesium has higher pharmacological activity.

DETAILED DESCRIPTION OF THE PRESENT INVENTION

Figure 1:
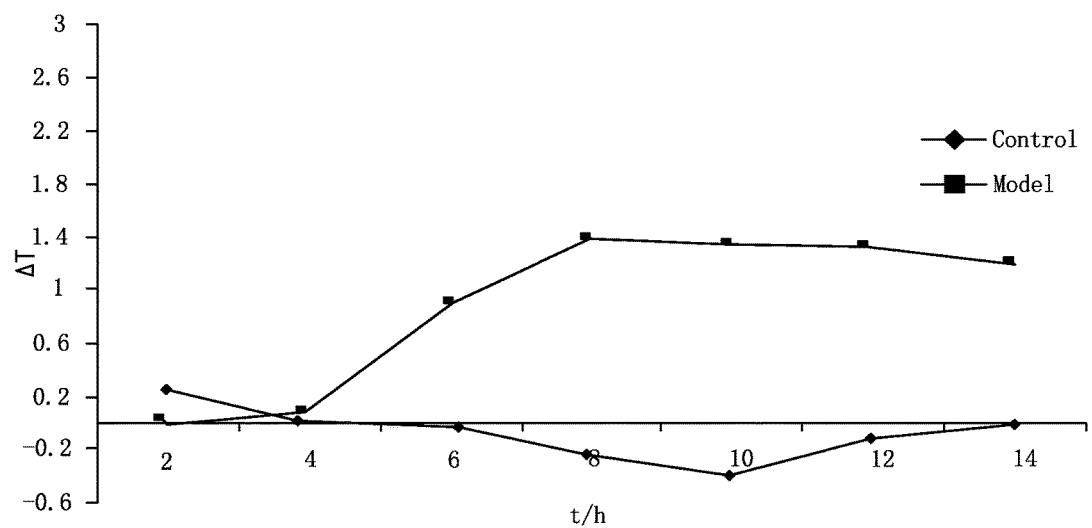
FIG. 1 is a graph showing changes in body temperature of yeast-induced febrile rats.

The present invention will be better understood by the following embodiments.

Example 1: Preparation of Baicalin Magnesium Compound

This embodiment was implemented by the following steps.
A. Preparation of Baicalin Suspension
Baicalin powder was added into purified water at a ratio of baicalin in grams to the purified water in milliliters of 1:30, and mixed uniformly to obtain a baicalin suspension.

B. Preparation of Magnesium Ion-Containing Baicalin Suspension
Magnesium hydroxide was added in the baicalin suspension obtained in step A at a molar ratio of baicalin to magnesium of 1.0:1.0, and mixed uniformly to obtain a magnesium ion-containing baicalin suspension.
C. Reaction
The magnesium ion-containing baicalin suspension obtained in step B was reacted at 30° C. under stirring until the reaction system became clear, and then filtered with a reduced-pressure filter device equipped with a Buchner funnel to obtain a filtrate.
D. Drying
The filtrate obtained in step C was heated and evaporated at 60° C. by HF881-2 Drying Oven (Wujiang Huafei Electric Heating Equipment Co., Ltd.) to obtain a baicalin magnesium compound having a moisture content of 1.0% by weight or less.

Example 2: Preparation of Baicalin Magnesium Compound

This embodiment was implemented by the following steps.
A. Preparation of Baicalin Suspension
Baicalin powder was added into purified water at a ratio of baicalin in grams to the purified water in milliliters of 1:50, and mixed uniformly to obtain a baicalin suspension.
B. Preparation of Magnesium Ion-Containing Baicalin Suspension
Magnesium oxide compound was added in the baicalin suspension obtained in step A at a molar ratio of baicalin to magnesium of 2.0:1.0, and mixed uniformly to obtain a magnesium ion-containing baicalin suspension.
C. Reaction
The magnesium ion-containing baicalin suspension obtained in step B was reacted at 70° C. under stirring until the reaction system became clear, and then filtered by a reduced-pressure filter device equipped with a Buchner funnel to obtain a filtrate.
D. Drying
The filtrate obtained in step C was spray-dried by QZR-5 Spray Drying Device (Linzhou Drying Machine Company, Xishan, Jiangsu) to obtain baicalin magnesium having a moisture content of 1.0% by weight or less.

Example 3: Preparation of Baicalin Magnesium Compound

This embodiment was implemented by the following steps.
A. Preparation of Baicalin Suspension
Baicalin powder was added into purified water at a ratio of baicalin in grams to the purified water in milliliters of 1:20, and mixed uniformly to obtain a baicalin suspension.
B. Preparation of Magnesium Ion-Containing Baicalin Suspension
Basic magnesium carbonate was added in the baicalin suspension obtained in step A at a molar ratio of baicalin to magnesium of 0.5:1.0, and mixed uniformly to obtain a magnesium ion-containing baicalin suspension s.
C. Reaction
The magnesium ion-containing baicalin suspension obtained in step B was reacted at 60° C. under stirring until the reaction system became clear, and then filtered by a reduced-pressure filter device equipped with a Buchner funnel to obtain a filtrate.

D. Drying

The filtrate obtained in step C was freeze-dried at −40° C. by EYELA OSB-2100 Freeze Drying Device (Beijing Oriental Science & Technology Development Co., Ltd.) to obtain a baicalin magnesium compound having a moisture content of 1.0% by weight or less.

Example 4: Preparation of Baicalin Magnesium Compound

This embodiment was implemented by the following steps.

A. Preparation of Baicalin Suspension

Baicalin powder was added into purified water at a ratio of baicalin in grams to the purified water in milliliters of 1:20, and mixed uniformly to obtain a baicalin suspension.

B. Preparation of Magnesium Ion-Containing Baicalin Suspension

Magnesium sulfate was added in the baicalin suspension obtained in step A at a molar ratio of baicalin to magnesium of 0.5:1.0, and mixed uniformly to obtain a magnesium ion-containing baicalin suspension s.

C. Reaction

The suspension containing magnesium ions obtained in step B was reacted at 70° C. under stirring until the reaction system became clear, and then filtered by a reduced-pressure filter device equipped with a Buchner funnel to obtain a filtrate.

D. Drying

The filtrate obtained in step C was spray-dried by QZR-5 Spray Drying Device (Linzhou Drying Machine Company, Xishan, Jiangsu), to obtain a baicalin magnesium compound having a moisture content of 1.0% by weight or less.

Example 5: Preparation of Baicalin Magnesium Compound

This embodiment was implemented by the following steps.

A. Preparation of Baicalin Suspension

Baicalin powder was added into purified water at a ratio of baicalin in grams to the purified water in milliliters of 1:100, and mixed uniformly to obtain a baicalin suspension.

B. Preparation of Magnesium Ion-Containing Baicalin Suspension

Magnesium nitrate was added in the baicalin suspension obtained in step A at a molar ratio of baicalin to magnesium of 2.0:1.0, and mixed uniformly to obtain a magnesium ion-containing baicalin suspension.

C. Reaction

The suspension containing magnesium ions obtained in step B was reacted at 60° C. under stirring until the reaction system became clear, and then filtered by a reduced-pressure filter device equipped with a Buchner funnel to obtain a filtrate.

D. Drying

The filtrate obtained in step C was freeze-dried at −40° C. with EYELA OSB-2100 Freeze Drying Device (Beijing Oriental Science & Technology Development Co., Ltd.) to obtain a baicalin magnesium compound having a moisture content of 1.0% by weight or less. Compound

Example 6: Preparation of Baicalin Magnesium Compound

This embodiment was implemented by the following steps.

A. Preparation of Baicalin Suspension

Baicalin powder was added into purified water at a ratio of baicalin in grams to the purified water in milliliters of 1:30, and mixed uniformly to obtain a baicalin suspension.

B. Preparation of Magnesium Ion-Containing Baicalin Suspension

Magnesium chloride was added in the baicalin suspension obtained in step A at a molar ratio of baicalin to magnesium of 1.0:1.0, and mixed uniformly to obtain a magnesium ion-containing baicalin suspension.

C. Reaction

The suspension containing magnesium ions obtained in step B was reacted at 50° C. under stirring until the reaction system became clear, and then filtered by a reduced-pressure filter device equipped with a Buchner funnel to obtain a filtrate.

D. Drying

The filtrate obtained in step C was freeze-dried at −40° C. by EYELA OSB-2100 Freeze Drying Device (Beijing Oriental Science & Technology Development Co., Ltd.) to obtain a baicalin magnesium compound having a moisture content of 1.0% by weight or less.

Example 7: Preparation of Baicalin Magnesium Compound

The preparation method includes the following steps.

A. Pretreatment of Macroporous Resin

HPD-100 macroporous resin (Zhengzhou Qinshi Science & Technology Co., Ltd.) was soaked in a 95 vol % ethanol solution for 26 hours, and packed in a column in a wet manner to allow the 95 vol % ethanol solution pass through macroporous resin column at a rate of 1.5 BV/h until a liquid from the macroporous resin column and water mixed at a ratio of 1:5 by volume was no longer white and cloudy; and the macroporous resin column was eluted to colorless with distilled water at a rate of 1.7 BV/h.

B. Extraction

Radix scutellariae was added in a 50 vol % ethanol solution at a ratio of the radix scutellariae in grams to the ethanol aqueous solution in milliliters of 1:11, then extracted under stirring at 60° C. for 1.0 hour, and separated to obtain a solution and a residue; the residue was repetitively extracted 2 times under the same conditions to produce multiple extracts; and the multiple extracts were combined to obtain a radix scutellariae extract.

C. Adsorption and Elution

The radix scutellariae extract obtained in step B was passed through the macroporous resin column pretreated in step A at a rate of 1.5 BV/h for adsorption; the macroporous resin column was washed with water of 4 times the volume of a macroporous resin bed; and the macroporous resin column was eluted with 50 vol % ethanol solution having 4 times the macroporous resin bed to collect a baicalin-containing eluent.

D. Concentration and Drying

The baicalin-containing eluent obtained in step C was concentrated at 0.01 MPa and at 50° C. with R2002 Rotary Evaporator (Shanghai Shenshun Biotechnology Co., Ltd.) until a concentrate had a volume of 1 times the weight in grams of the radix scutellariae; and then the concentrate was heated and evaporated at 60° C. by HF881-2 drying oven (Wujiang Huafei Electric Heating Equipment Co., Ltd.) to obtain a crude baicalin magnesium extract.

E. Purification

The crude baicalin magnesium extract obtained in step D was recrystallized and purified with 80% ethanol at 60° C. to obtain the baicalin magnesium compound.

Example 8: Preparation of Baicalin Magnesium Compound

The preparation method includes the following steps.

A. Pretreatment of Macroporous Resin

AB-8 macroporous resin (Zhengzhou Qinshi Science & Technology Co., Ltd.) was soaked in a 95 vol % ethanol solution for 20 hours, and packed in a column in a wet manner to allow the 95 vol % ethanol solution pass through macroporous resin column at a rate of 2.5 BV/h until a liquid from the macroporous resin column and water mixed at a ratio of 1:5 by volume was no longer white and cloudy; and the macroporous resin column was eluted to colorless with distilled water at a rate of 1.5 BV/h.

B. Extraction

Radix scutellariae was added in a 40 vol % ethanol solution at a ratio of the radix scutellariae in grams to the ethanol aqueous solution in milliliters of 1:8, then extracted under stirring at 55° C. for 1.5 hours, and separated to obtain a solution and a residue; the residue was repetitively extracted 3 times under the same conditions to produce multiple extracts; and the multiple extracts were combined to obtain a radix scutellariae extract.

C. Adsorption and Elution

The radix scutellariae extract obtained in step B was passed through the macroporous resin column pretreated in step A at a rate of 2.5 BV/h for adsorption; the macroporous resin column was washed with water of 5 times the volume of a macroporous resin bed; and the macroporous resin column was eluted with 45 vol % ethanol solution of 5 times the macroporous resin bed to collect a baicalin-containing eluent.

D. Concentration and Drying

The baicalin-containing eluent obtained in step C was concentrated at 0.03 MPa and at 35° C. with R2002 Rotary Evaporator (Shanghai Shenshun Biotechnology Co., Ltd.) until a concentrate had a volume of 15 times the weight in grams of the radix scutellariae; and then the concentrate was spray-dried at 60° C. by QZR-5 spray drying device (Linzhou Drying Machine Company, Xishan, Jiangsu) to obtain a crude baicalin magnesium extract.

E. Purification

The crude baicalin magnesium extract obtained in step D was purified using 10-40% of methanol-water as eluent by GEL C18 AAG12S50 ODS column (YMC Company) to obtain the baicalin magnesium compound.

Example 9: Preparation of Baicalin Magnesium Compound

The preparation method includes the following steps.

A. Pretreatment of Macroporous Resin

D-101 macroporous resin (Zhengzhou Xidian Electric Power Resin Sales Co., Ltd.) was soaked in a 95 vol % ethanol solution for 28 hours, and packed in a column in a wet manner to allow the pass through macroporous resin column at a rate of 2.2 BV/h until a liquid from the macroporous resin column and water mixed at a ratio of 1:5 by volume was no longer white and cloudy; and the macroporous resin column was eluted to colorless with distilled water at a rate of 2 BV/h.

B. Extraction

Radix scutellariae was added in a 60 vol % ethanol solution at a ratio of the radix scutellariae in grams to the ethanol aqueous solution in milliliters of 1:12, then extracted under stirring at 65° C. for 1.0 hour, and separated to obtain a solution and a residue; the residue was repetitively extracted 2 times under the same conditions to produce multiple extracts; and the multiple extracts were combined to obtain a radix scutellariae extract.

C. Adsorption and Elution

The radix scutellariae extract obtained in step B was passed through the macroporous resin column pretreated in step A at a rate of 2.0 BV/h for adsorption; the macroporous resin column was washed with water of 4 times the volume of a macroporous resin bed; and the macroporous resin column was eluted with 55 vol % ethanol solution of 6 times the macroporous resin bed to collect a baicalin-containing eluent.

D. Concentration and Drying

The baicalin-containing eluent obtained in step C was concentrated at 0.1 MPa and at 65° C. with R2002 rotary evaporator (Shanghai Shenshun Biotechnology Co., Ltd.) until a concentrate had a volume of 5 times the weight in grams of the radix scutellariae; and then the concentrate was spray-dried at −40° C. by LGJ-22D freeze drying device (Beijing Four-Ring Scientific Instrument Co., Ltd.) to obtain a crude baicalin magnesium extract.

E. Purification

The crude baicalin magnesium extract obtained in step D was purified with Innoval C18 Preparative Liquid Chromatographic Column (Bonna-Agela Technologies) under methanol-water of 30:70 to obtain the baicalin magnesium compound.

Example 10: Preparation of Baicalin Magnesium Compound

The preparation method includes the following steps.

A. Pretreatment of Macroporous Resin

YWD06B macroporous resin (Zhengzhou Qinshi Science & Technology Co., Ltd.) was soaked in a 95 vol % ethanol solution for 24 hours, and packed in a column in a wet manner to allow the pass through macroporous resin column at a rate of 2.0 BV/h until a liquid from the macroporous resin column and water mixed at a ratio of 1:5 by volume was no longer white and cloudy; and the macroporous resin column was eluted to colorless with distilled water at a rate of 2.5 BV/h.

B. Extraction

Radix scutellariae was added in a 45 vol % ethanol solution at a ratio of the radix scutellariae in grams to the ethanol aqueous solution in milliliters of 1:9, then extracted under stirring at 65° C. for 1.0 hour, and separated to obtain a solution and a residue; the residue was repetitively extracted 3 times under the same conditions to produce multiple extracts; and the multiple extracts were combined to obtain a radix scutellariae extract.

C. Adsorption and Elution

The radix scutellariae extract obtained in step B was passed through the macroporous resin column pretreated in step A at a rate of 2.0 BV/h for adsorption; the macroporous resin column was washed with water of 5 times the volume of a macroporous resin bed; and the macroporous resin column was eluted with 55 vol % ethanol solution of 5 times the volume of the macroporous resin bed to collect a baicalin-containing eluent.

D. Concentration and Drying

The baicalin-containing eluent obtained in step C was concentrated at 0.07 MPa and at 45° C. with R2002 Rotary Evaporator (Shanghai Shenshun Biotechnology Co., Ltd.) until a concentrate had a volume of 10 times the weight in grams of the radix scutellariae; and then the concentrate was spray-dried at −40° C. by QZR-5 Spray Drying Device (Linzhou Drying Machine Company, Xishan, Jiangsu) to obtain a crude baicalin magnesium extract.

E. Purification

The crude baicalin magnesium extract obtained in step D was purified using 10-40% of methanol-water as eluent by GEL C18 AAG12S50 ODS column (YMC Company) to obtain the baicalin magnesium compound.

Pharmacological Test 1: Protection Against Liver Injury 40 healthy mice were randomly divided into 4 groups, a normal group, a model group, a baicalin group and a baicalin magnesium group. Mice in the baicalin group were administrated with baicalin at a dose of 10 mg/kg, and mice in the baicalin magnesium group were administrated with baicalin magnesium at a dose equivalent to 10 mg/kg of baicalin. Mice in the normal group and the model group were intragastrically administrated with the same volume of normal saline for 5 days. On the fourth day, mice in the model group and the administration groups were intraperitoneally injected with 0.5 g/kg of D-galactose, and mice in the normal group were intraperitoneally injected with the same volume of normal saline. The activities of ALT, AST, SOD and GSH-Px in the serum and the content of MDA were detected. Variance analysis was performed by SPSS-19.0 statistical software. The results were shown in Table 5.

TABLE 5

Results of the protective effects on the liver injury

| Groups | ALT (U/L) | AST (U/L) | SOD (U/L) | GSH-Px (U/L) | MDA (nmol/L) |
|---|---|---|---|---|---|
| Normal | 97.6 ± 9.3* | 76.6 ± 9.1* | 47.4 ± 6.3* | 11.6 ± 2.4* | 1.7 ± 0.4* |
| Model | 320.5 ± 50.6 | 297.6 ± 39.3 | 27.2 ± 3.4 | 7.7 ± 0.4 | 4.3 ± 0.6 |
| Baicalin | 191.4 ± 19.4* | 168.5 ± 11.9* | 45.2 ± 2.9* | 9.8 ± 0.9* | 3.1 ± 0.4* |
| Baicalin Magnesium | 165.1 ± 8.7*$^\Delta$ | 139.8 ± 13.7*$^\Delta$ | 48.2 ± 2.9* | 11.8 ± 0.5*$^\Delta$ | 2.1 ± 0.3*$^\Delta$ |

Notes:
*$P < 0.05$ in comparison to the model group; and $^\Delta P < 0.05$ in comparison to the baicalin group.

The results in Table 5 indicate that the baicalin and the baicalin magnesium groups significantly reduce the elevation of serum ALT and AST in mice with acute liver injury induced by D-galactose, and increase the activity of SOD and GSH-Px and decrease the content of MDA ($P<0.05$); and as compared to the baicalin group, the elevation of serum ALT and AST in mice with acute liver injury induced by D-galactose more significantly reduced in the baicalin magnesium group; and the activity of SOD and GSH-Px is increased, and the content of MDA is reduced more significantly ($P<0.05$) in the baicalin magnesium group.

Pharmacological Test 2: Effect on Learning and Memory Function in Mice with Cerebral Ischemia 80 healthy mice were randomly divided into 4 groups each having 20 mice, a model group, a sham-operation group, a baicalin group and a baicalin magnesium group.

For the model group, mice were intraperitoneally injected with 1% of pentobarbital sodium for anesthesia, and then the left and right common carotid arteries were exposed and separated. The left and right arteries were immediately clipped with a vessel clamp for 20 minutes. The vessel clamp then were released; arteries were sutured; and the mice were put back in the cage for breeding. For the sham-operation group, the left and right common carotid arteries were exposed by the same method as above but without clipping. The left and right arteries were sutured, and the mice were put back in the cage for breeding. For the baicalin group, the operation was the same as that for the model group, and on the second day after the operation the mice were intraperitoneally injected with 12.5 mg/kg of baicalin for successive 12 days. For the baicalin magnesium group, the operation was the same as that for the model group, and on the second day after the operation the mice were intraperitoneally injected with baicalin magnesium (at a dose equivalent to 12.5 mg/kg of baicalin) for successive 12 days. The mice in the sham-operation group and the model group were administrated with the same volume of normal saline.

Water Maze Test: a circular water tank for test was 120 cm in diameter and 60 cm in height; a cylindrical platform was 10 cm in diameter and 40 cm in height; and an interior of the circular water tank was black. A camera connected to a display was provided to record the movement of mice. During the test, the water depth was 12 cm, and the water temperature was (25±2) ° C. All space signs around the maze remained unchanged throughout the test.

Water Maze Test for Memory: on the day before the beginning of the test, each of mice were familiar with the water environment in the maze for 2 minutes. The mice were randomly placed in water close to walls of maze from four different quadrants (North, West, South and East, in one period of time), and the time from the mice entering water to climbing on the platform was recorded as an escape latency. For the mice that did not find the platform within 120 seconds, the latency was recorded as 120 seconds, whiling guiding them to find the platform and have a rest for 60 seconds. The mice were continuously trained for 15 days at a frequency of two times of training per day. Each group of animals was subjected to a water maze test in turn. The path on the first day had two blind ends; the path on the second day had three blind ends; and the path on the third day, the fourth day and the fifth day had four blind ends. The mice were placed in water toward the walls, and the time from the mice entering water to arriving at the platform (latency) and the number of entering the blind ends were recorded. If the mice did not arrive at the platform within 60 seconds, the mice may be guided to the platform and were allowed to stay on the platform for 20 seconds. The mice were trained in the morning and afternoon per day, total 5 days.

The test data were expressed by mean±standard deviation (x̄±s), and single-factor variance analysis was performed on the data with SPSS19.0 statistical software. $P<0.05$ was of statistical significance.

TABLE 6

Protection against learning and memory impairment in mice with cerebral ischemia

| Groups | Escape Latency (s) | Number of Errors |
|---|---|---|
| Model | 57.53 ± 13.65 | 8.56 ± 2.56 |
| Sham-operation | 24.63 ± 7.9* | 2.32 ± 1.56* |

TABLE 6-continued

Protection against learning and memory impairment in mice with cerebral ischemia

| Groups | Escape Latency (s) | Number of Errors |
|---|---|---|
| Baicalin | 38.88 ± 11.99* | 4.56 ± 3.78* |
| Baicalin Magnesium | 26.54 ± 8.34*$^\Delta$ | 3.82 ± 2.12*$^\Delta$ |

Notes:
*$P < 0.05$ in comparison to the model group; and $^\Delta P < 0.05$ in comparison to the baicalin group.

The results in Table 6 indicate that the escape latency of mice learning from water maze training in the baicalin group and the baicalin magnesium group is significantly reduced and the number of errors is also reduced, which is of statistical significance as compared to the model group; and the escape latency and number of errors in the baicalin magnesium group is significantly reduced, which is of statistical significance as compared to the baicalin group.

Pharmacological Test 3: Anti-Inflammatory Activity 144 healthy mice were randomly divided into 3 groups, a baicalin group, a baicalin magnesium group and a control group. Each group was divided into six subgroups each having 8 mice according to time points (1 h, 3 h, 5 h, 7 h, 11 h and 15 h). Mice in the baicalin group were orally administrated (ig administration) at a dose of 100 mg·kg-1; mice in the baicalin magnesium group were orally administrated (ig administration) at a dose equivalent to 100 mg·kg-1 of baicalin; and mice in the control group were administrated with the same volume of normal saline. At 40 minutes before each time point, 100 μl of xylene was dropped in left ears of the mice in each group; when at a time point, the animals were sacrificed. Auricles of both ears of the mice were obtained with a puncher, and the difference in weight (swelling degree) between the left ear and the right ear was used as an indication of the anti-inflammatory effect of the drug. The results were shown in Table 7.

TABLE 7

Time-response relationship of inhibition effects of baicalin and baicalin magnesium on the xylene-induced ear swelling in mice (n = 8)

| Groups | Baicalin (mg) | Baicalin Magnesium (mg) |
|---|---|---|
| 1 h | 7.57 ± 3.05 | 5.87 ± 2.05*$^\Delta$ |
| 3 h | 4.66 ± 2.76* | 4.57 ± 3.56* |
| 5 h | 4.88 ± 1.99* | 4.63 ± 2.78* |
| 7 h | 6.77 ± 2.54* | 5.87 ± 3.43* |
| 11 h | 7.89 ± 2.98 | 6.77 ± 3.75*$^\Delta$ |
| 15 h | 9.12 ± 1.98 | 7.97 ± 2.85$^\Delta$ |

Notes:
*$P < 0.05$ in comparison to the normal control group (10.25 ± 3.15); and $^\Delta P < 0.05$ in comparison to the baicalin group.

The results in Table 7 indicate that both the baicalin group and the baicalin magnesium group may significantly inhibit the xylene-induced ear swelling in mice; after administration for 1 hour, the baicalin magnesium group shows greater anti-inflammatory effect than the baicalin group, and the difference is significant. The results indicate that the anti-inflammatory effect of the baicalin magnesium comes into play early and stable with longer retention time and faster absorption.

Pharmacological Test 4: Anti-Tumor Activity

Human liver cancer HepG2 cells were prepared and then cultured in an incubator containing 5% of $CO_2$ at 37° C. using a DMEN culture medium containing 10% of fetal bovine serum, penicillin (100 μmol·L$^{-1}$) and streptomycin (1 mg·mL$^{-1}$).

HepG2 cells in logarithmic phase were diluted with RPMI-1640 culture medium containing 10% of fetal bovine serum to a concentration of 1×104 per mL; then inoculated into a 96-well plate at 100 μL per well; and then cultured in an incubator having a relative humidity of 90% and 5% of $CO_2$ at 37° C. The culture medium was discarded after the HepG2 cells were cultured for 24 hours. The culture medium containing baicalin and baicalin magnesium (equivalent to the concentration of baicalin (5 μg/mL, 10 μg/mL and 20 μg/mL)) were added in wells respectively with each concentration in four parallel wells. And at the same time, wells having culture medium without cells were used as a blank control group, and wells having cells without drug were used as a negative control group. The groups were continuously cultured for 48 hours to collect the cells. The cells were washed with PBS solution 2 times, and detected with a flow cytometer by FACS for parameter acquisition and data analysis. The results were shown in Table 8.

TABLE 8

Effect of baicalin and baicalin magnesium on apoptosis of human liver cancer HepG2 cells

| Groups | Concentration (μg/mL) | Apoptosis % |
|---|---|---|
| Control | — | 1.17 ± 0.15 |
| Baicalin | 5 | 9.57 ± 0.56* |
|  | 10 | 21.45 ± 1.67* |
|  | 20 | 30.67 ± 3.45* |
| Baicalin Magenesium | 5 | 11.67 ± 0.65* |
|  | 10 | 23.67 ± 5.21* |
|  | 20 | 33.12 ± 1.58*$^\Delta$ |

Notes:
*$P < 0.05$ in comparison to the control group; and $^\Delta P < 0.05$ in comparison to the baicalin group.

The results in Table 8 indicate that the different degrees of apoptosis of liver cancer HepG2 cells occur after being treated by the baicalin solution and the baicalin magnesium solution having a concentration of 5 μg/mL, 10 μg/mL or 20 μg/mL for 48 hours; and the baicalin magnesium of the same concentration has more significant effects on the cell apoptosis than the baicalin. The results have statistical differences.

Pharmacological Test 5: Effect on Analgesia in Mice 40 mice, 20-22 g in weight, were randomly divided into 4 groups each having 10 mice, a baicalin (0.067 g/kg) group, a baicalin magnesium (equivalent to 0.067 g/kg of baicalin) group, a blank control group (administrated with normal saline), and an aspirin positive control group (0.15 g/kg). The mice were intragastrically administrated once per day for successive 7 days. After 30 minutes of final administration, the mice were intraperitoneally injected with 0.6% acetic acid saline solution at a dose of 0.2 mL/10 g; the number of writhing responses in the mice within 15 minutes was counted. Analgesia % was calculated as follows:

Analgesia %=[(average number of writhing responses of the blank control group–average number of writhing responses of the drug administration group)/average number of writhing responses of the blank control group]× 100%.

Single-factor variance analysis was performed on data by the SPSS19.0 statistical software, and P<0.05 was of statistical significance. The results were shown in Table 9.

TABLE 9

Influences of baicalin and baicalin magnesium on acetic acid-induced pain in mice

| Groups | Dose (g/kg) | Number of writhing | Analgesia % |
|---|---|---|---|
| Blank Control | — | 26.45 ± 7.50 | |
| Positive Control | 0.15 | 4.43 ± 3.21* | 83.3* |
| Baicalin | 0.067 | 17.54 ± 4.44* | 33.7* |
| Baicalin Magnesium | 0.067 | 10.43 ± 3.56*△ | 60.6*△ |

Notes:
*$P < 0.05$ in comparison to the control group; and $^{\triangle}P < 0.05$ in comparison to the baicalin group.

The results in Table 9 indicate that the baicalin magnesium group has more obvious inhibition effects on the acetic acid induced pain in mice than the blank control group, and has better effects than the baicalin group.

Pharmacological Test 6: Antipyretic Effect

SD male rats were randomly divided into 4 groups, a control group, a model group, a baicalin group and a baicalin magnesium group. Rats were raised in a normal day/night cycle and at room temperature (22±2° C.) and a relative humidity of (50±2)%. Three days before the test, rats were placed in the experimental environment to adapt to the experimental conditions. Rats having a basal body temperature of 37.5-39.0° C. were selected for test The rats were fasted for 12 hours before the test, and the body temperature of rats was measured once every 1 hour when tested. Average of three body temperature values (the temperature values would be removed if a difference between the highest value and the lowest value was greater than 0.5° C.) of rats was used as the basal body temperature.

The rats were intragastrically administered with baicalin or baicalin magnesium, and then immediately subcutaneously injected with 20% of dried yeast saline suspension (not for the control group). The administration mode was as follows: rats in the control group were intragastrically administered with 2 ml/kg of normal saline and subcutaneously injected with 10 ml/kg of normal saline; rats in the model group were ntragastrically administered 2 ml/kg of normal saline and subcutaneously injected with 2 g/kg of yeast; rats in the baicalin group were intragastrically administrated with 80 mg/kg of baicalin and subcutaneously injected with 2 g/kg of yeast; and rats in the baicalin magnesium group were intragastrically administrated with baicalin magnesium (equivalent to 80 mg/kg of baicalin) and subcutaneously injected with 2 g/kg of yeast. The body temperature of the rats was measured once every 2 hours for 14 hours to observe the temperature change of rats ($\Delta T$, ° C.) at different time after injection of the yeast. The results were shown in FIG. 1 and FIG. 2.

Figure 2:
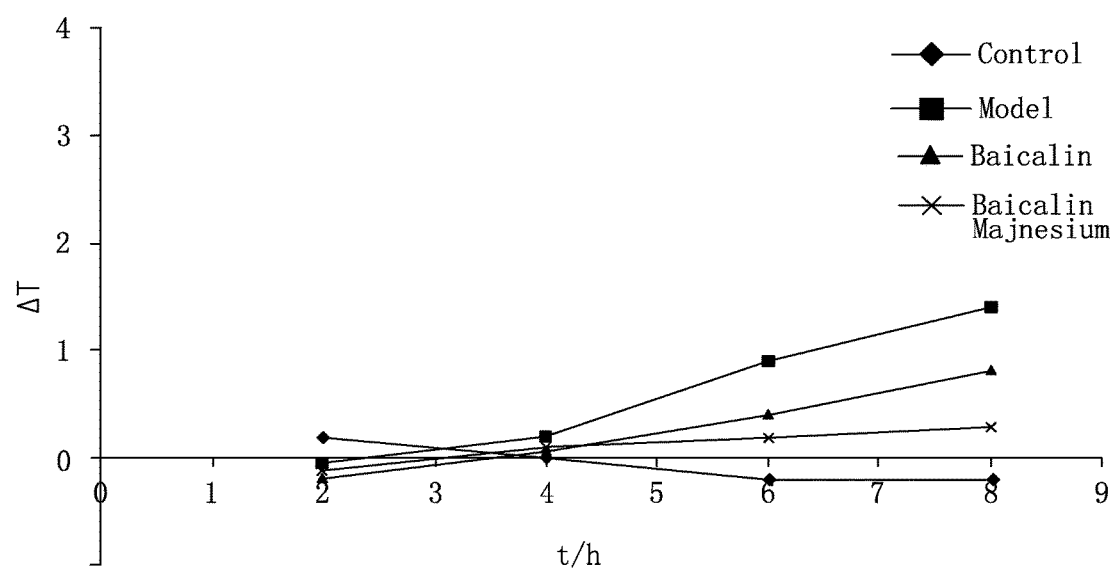
FIG. 2 is graph showing the effect of baicalin on yeast-induced febrile rats.

The results in FIG. 1 indicate that the rats in the model group had a peak temperature within 8 hours after subcutaneous injection of the yeast suspension; $\Delta T$ was 1.4° C.; and the effect lasted for 14 hours or more. FIG. 2 indicates that the body temperatures of the rats in the control group had no obvious change during the test. For the rats in the model group after subcutaneous injection of yeast suspension, $\Delta T$ at 6 h and 8 h was 0.95° C. and 1.4° C., respectively; and the increase in body temperature of rats was of great significance in comparison to the control group ($P<0.05$). At 6 h, $\Delta T$ in the baicalin group and the baicalin magnesium group was 0.4° C. and 0.2° C., respectively, which were obviously reduced in comparison to the model group ($P<0.05$); at 8 h, $\Delta T$ in the baicalin group and the baicalin magnesium group was 0.8° C. and 0.3° C., respectively, which were obviously reduced in comparison to the model group ($P<0.05$); and, by comparing the baicalin magnesium with the baicalin, $\Delta T$ at 6 h and 8 h was 0.2° C. and 0.5° C., respectively. The results indicate that the baicalin inhibits or intervenes the yeast-induced fever, and the baicalin magnesium more effective.

Pharmacological Test 7: Antidiabetic Effect

Healthy SD male rats aged 6 to 8 weeks were randomly divided into 4 groups, a high-fat diet control group, a diabetes control group, a baicalin treatment group and a baicalin magnesium treatment group. The rats were raised for 1 week in advance. In the second week, all rats were fed with high-fat diet. After six weeks, the rats were fasted but with water for 12 hours. For the diabetes control group, the baicalin treatment group and the baicalin magnesium treatment group, rats were administrated by tail vein injection with 45 mg/kg of streptozotocin prepared from citrate buffer solution (pH=4.5). After 3 to 7 days, the fasting blood glucose was measured. The blood glucose level greater than 13 mmol/L was a criterion for the successful diabetes rate model. The rats in the high-fat diet control group were administrated by tail vein injection with the citrate buffer solution.

After the model was built, the rats were intragastrically administered in the morning every day. The rats in the baicalin group were administrated with baicalin at a dose of 80 mg/kg; the rates in the baicalin group were administrated with baicalin magnesium at a dose equivalent to 80 mg/kg of baicalin; and the rats in the diabetes model group and the high-fat diet control group were intragastrically administrated the same volume of solvent once every day and for successive 6 weeks. After the molding and the administration, the blood glucose was measured in the third week and the sixth week. Single-factor variance analysis was performed on data by SPSS19.0 statistical software, and $P<0.05$ was of statistical significance. The results were shown in Table 10.

TABLE 10

Effects of baicalin and baicalin magnesium on blood glucose with streptozotocin-induced diabetes in mice.

| Groups | Blood Glucose (mmol/L) 0 | 3 weeks | 6 weeks |
|---|---|---|---|
| Control | 9.10 ± 0.5 | 6.85 ± 0.3 | 7.86 ± 0.4 |
| Diabetes Model | 21.96 ± 3.8* | 23.14 ± 3.56* | 25.12 ± 6.9* |
| Baicalin | 23.54 ± 2.5* | 21.45 ± 2.6* | 20.14 ± 2.6* |
| Baicalin Magnesium | 22.32 ± 2.23* | 19.46 ± 3.59*△# | 17.58 ± 2.6*△# |

Notes:
*$P < 0.05$ in comparison to the control group; $^{\triangle}P < 0.05$ in comparison to the baicalin group; and $^{\#}P < 0.05$ in comparison to the model group.

The results in Table 10 indicated that in the third week of the test, the blood glucose of the rats in the diabetes model group was increased, and the blood glucose of the rats in the baicalin group and the baicalin magnesium group was reduced. In the sixth week, the blood glucose of the rats in the diabetes model group was still increased, the blood glucose of the rats in the baicalin group and the baicalin magnesium group was further reduced, and the blood glucose of the rats in the baicalin group and the baicalin magnesium group was obviously lower than that of the diabetes model group ($P<0.05$), indicating the baicalin can improve the symptoms of the diabetes. Meanwhile, the reduction in the blood glucose of the rats in the baicalin magnesium group was obviously greater than that of the baicalin group ($P<0.05$).

Experimental Embodiment: Comparison of Baicalin and Baicalin Magnesium in Water Solubility The solubility of the baicalin and the solubility of the baicalin magnesium in water at 37° C. were measured by a conventional solubility measurement method. The results were shown in Table 11.

TABLE 11

Water solubility of baicalin and baicalin magnesium

| Samples | Solubility (mg/mL) |
|---|---|
| Baicalin | 0.058 |
| Baicalin magnesium | 129.1 |

The results in Table 1 indicate that the baicalin magnesium has better water solubility, which is 2225 times the solubility of the baicalin.

What is claimed is:

1. A baicalin magnesium compound of formula (I):

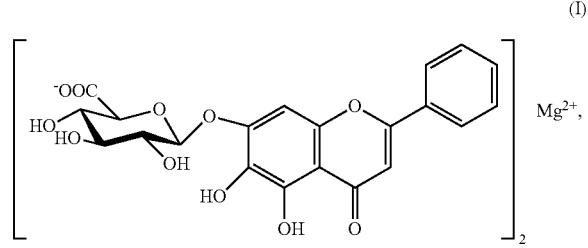

2. A method for preparing the baicalin magnesium compound of claim 1, comprising:
   a. adding baicalin powder to purified water at a weight (g)-volume (ml) ratio of 1:20-100 of the baicalin to the purified water; and uniformly mixing the baicalin powder and the purified water to obtain a baicalin suspension;
   b. adding a magnesium compound in the baicalin suspension obtained in step A at a molar ratio of baicalin to magnesium of 0.5-3.0:1; and uniformly mixing the magnesium compound and the baicalin suspension to obtain a magnesium ion-containing baicalin suspension;
   c. reacting the magnesium ion-containing baicalin suspension obtained in step B at 20-70° C. under stirring until the reaction system becomes clear; and then filtering the magnesium ion-containing baicalin suspension to obtain a filtrate; and
   d. drying the filtrate obtained in step C to produce the baicalin magnesium compound.

3. The method of claim 2, wherein the magnesium compound is selected from the group consisting of magnesium hydroxide, magnesium oxide, basic magnesium carbonate, magnesium acetate, magnesium sulfate, magnesium nitrate and magnesium chloride.

4. The method of claim 2, wherein in step D, the drying is heating to evaporate, spray drying or freeze drying.

5. The method of claim 2, wherein the baicalin magnesium compound obtained in step D is purified by recrystallization, octadecyl silane reversed-phase column chromatography or preparative liquid chromatography until the baicalin magnesium compound has a content of 95% by weight or more.

6. A method for preparing the baicalin magnesium compound of claim 1, comprising:
   a. soaking a macroporous resin in a 95 vol % ethanol solution for 20-28 hours; packing the soaked macroporous resin on a column in a wet manner to allow the 95 vol % ethanol solution to pass through macroporous resin column at a rate of 1.5-2.5 BV/h until a liquid from the macroporous resin column and water mixed at a ratio of 1:5 by volume is no longer white and cloudy; and eluting the macroporous resin column to colorless with distilled water at a flow rate of 1.5-2.5 BV/h;
   b. adding radix scutellariae in a 40-60 vol % ethanol solution at a weight (g)-volume (ml) ratio of 1:8-15 of the radix scutellariae to the 40-60 vol % ethanol solution; decocting under stirring at 55-65° C. for 0.8-1.2 hours to produce a mixture; filtering the mixture to obtain a solution and a residue; repeatedly subjecting the residue to extraction 2-3 times to produce multiple extracts; and combining the multiple extracts to obtain a radix scutellariae extract;
   c. passing the radix scutellariae extract obtained in step B through the macroporous resin column in step A at a rate of 1.5-2.5 BV/h for adsorption; washing the macroporous resin column with water of 4-6 times the volume of a macroporous resin bed; and eluting the macroporous resin column with 45-55 vol % ethanol solution of 4-6 times the volume of the macroporous resin bed to collect a baicalin-containing eluent;
   d. concentrating the baicalin-containing eluent obtained in step C at 35-65° C. under reduced pressure until a concentrate has a volume of 1-15 times the weight in grams of the radix scutellariae; and drying the concentrate to obtain a crude baicalin magnesium extract; and
   e. purifying the crude baicalin magnesium extract obtained in step D to produce the baicalin magnesium compound.

7. The method of claim 6, wherein the macroporous resin is selected from HPD-100, AB-8, D101 or YWD06B.

8. The method of claim 6, wherein the macroporous resin has a particle size of 10-80 mesh.

9. The method of claim 6, wherein a ratio of diameter to height of the macroporous resin column is 1:3-8.

10. The method of claim 6, wherein the drying is heating to evaporate, spray drying or freeze drying.

11. The method of claim 6, wherein the baicalin magnesium compound obtained in step E is purified by recrystallization, octadecyl silane reversed-phase column chromatography or preparative liquid chromatography until the baicalin magnesium compound has a content of 95% by weight or more.

12. A method of treating liver injury in a patient, comprising administering to the patient an effective amount of a composition comprising the baicalin magnesium compound of claim 1.

* * * * *